(12) United States Patent
Miyako et al.

(10) Patent No.: US 7,645,793 B2
(45) Date of Patent: Jan. 12, 2010

(54) INJECTABLE PHARMACEUTICAL FORMULATIONS

(75) Inventors: Yasuhiro Miyako, Osaka (JP); Hideaki Tai, Osaka (JP); Kazuichi Fujikane, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 245 days.

(21) Appl. No.: 10/483,772

(22) PCT Filed: Jul. 16, 2002

(86) PCT No.: PCT/JP02/07190

§ 371 (c)(1),
(2), (4) Date: Jan. 14, 2004

(87) PCT Pub. No.: WO03/007967

PCT Pub. Date: Jan. 30, 2003

(65) Prior Publication Data

US 2004/0162344 A1 Aug. 19, 2004

(30) Foreign Application Priority Data

Jul. 17, 2001 (JP) ............................. 2001-216617

(51) Int. Cl.
*A01N 37/12* (2006.01)
*A01N 37/44* (2006.01)
*A61K 31/24* (2006.01)
*C07C 229/00* (2006.01)

(52) U.S. Cl. .................... 514/534; 560/43; 562/441
(58) Field of Classification Search ............... 514/510, 514/534; 560/43; 562/441
See application file for complete search history.

(56) References Cited

U.S. PATENT DOCUMENTS

| | | | |
|---|---|---|---|
| 2,836,541 A * | 5/1958 | Lager ......................... | 514/282 |
| 4,604,377 A | 8/1986 | Fernandes et al. | |
| 5,089,503 A | 2/1992 | Johnson ..................... | 514/274 |
| 5,463,107 A * | 10/1995 | Konoike et al. ............... | 560/43 |
| 5,587,505 A * | 12/1996 | Konoike et al. ............. | 558/272 |
| 5,945,448 A * | 8/1999 | Ninomiya et al. ........... | 514/510 |
| 5,955,456 A | 9/1999 | Prato et al. ................... | 514/182 |
| 2003/0100507 A1* | 5/2003 | Gulati ......................... | 514/12 |

FOREIGN PATENT DOCUMENTS

| | | |
|---|---|---|
| EP | 0 261 426 | 3/1988 |
| EP | 04387474 * | 12/1990 |
| EP | 1 018 345 | 7/2000 |
| EP | 1 050 301 | 11/2000 |
| EP | 1050301 | 11/2000 |
| EP | 1 078 936 A2 | 2/2001 |
| JP | 61-165322 | 7/1986 |
| JP | 261426 | 3/1988 |
| JP | 63-225322 | 9/1988 |
| JP | 3-193735 | 8/1991 |
| JP | 07-053484 * | 2/1995 |
| JP | 7-53484 | 2/1995 |
| JP | 7-316188 | 12/1995 |
| JP | 9-124481 | 5/1997 |
| JP | 11-209277 | 8/1999 |
| JP | 2000-169372 | 6/2000 |
| JP | 2001-503781 | 3/2001 |
| JP | 2002-505282 | 2/2002 |
| WO | 96/38173 | 12/1996 |
| WO | 98/22136 | 5/1998 |
| WO | 99/44604 | 9/1999 |
| WO | 00/11023 | 3/2000 |
| WO | 00/61109 | 10/2000 |
| WO | 01/30804 | 5/2001 |

OTHER PUBLICATIONS

F.A. Alvarez Nunez et al., "Foaming activity and pK of some surface active compounds", International Journal of Pharmaceutics, vol. 151, No. 2, pp. 193-199, 1997.
T. Konoike et al., "Practical Large-Scale Synthesis of Endothelin Receptor Antagonist S-0139", Organic Process Research & Development, vol. 3, 1999, pp. 347-351.
Zeszyty naukowe uniwersytetu jagiellonskiego, prace chemiczne, 1964, No. 9, pp. 215-223.
B. Kamienski, "The Electric Surface Potential and Surface Tension of the m- and p-isomers of Hydroxybenzoic Acid Solutions and the Dissociation Constant", Bull, acad. polon, sci., ser. sci., chim., geol. et geograph, 1959, vol. 7, No. 2, pp. 97-100.
M. Paluch, "Electric Surface Potential and Surface Tension of Aqueous Solutions of ortho-Fluorobenzoic Acid", Bulletin de l'academie polonaise des sciences, serie des sciences chimiques, 1963, vol. 11, No. 2, pp. 97-100.
G. Pytasz, "Influence of Hydrogen Ion Concentration on Electric Surface Potential and Surface Tension of Pivalic Acid in Aqueous Solutions", Bulletin de l'academie polonaise des sciences, serie des sciences chimiques, 1965, vol. 13, No. 2, pp. 109-114.
B. Kamienski et al., "Surface Activity of Phenylhydrazine and its Chloro-Derivatives in Aqueous Solutions", Bulletin de l'academie polonaise des sciences, serie des sciences chimiques, 1971, vol. 19, No. 5, pp. 339-346.
B. Kamienski, et al., "Influence of Pyridine Amino Isomers on Electric Surface Potental and Surface Tension in Aqueous Solutions", Bulletin de l'academie polonaise des sciences, serie des sciences chimiques, 1967, vol. 15, No. 8, pp. 345-348.
B. Kamienski et al., "The Relationship between Surface Activity of a Substance and its Dissociation Constant", Bulletin de l'academie polonaise des sciences, serie des sciences chimiques, 1973, vol. 21, No. 7-8, pp. 581-585.
B. Kamienski, "On the Relation between Surface Phenomena and the Dissociation Constant of Weak Electrolytes in Aqueous Solution", Bull. intern. acad. polon. sci., classe sci. math. nat., 1937, 1937A, pp. 422-429.

(Continued)

Primary Examiner—Sreeni Padmanabhan
Assistant Examiner—Umamaheswari Ramachandran
(74) Attorney, Agent, or Firm—Wenderoth, Lind & Ponack, L.L.P.

(57) ABSTRACT

The present invention relates to a process for suppressing the foaming which may occur at the time of the preparation of a solution or a suspension. Particularly, the present invention relates to pharmaceuticals, foods, and the like wherein the foaming at the time of the preparation of a solution or a suspension, which may cause any disadvantage, is suppressed.

10 Claims, 2 Drawing Sheets

OTHER PUBLICATIONS

G. Zografi et al., "Interfacial Properties of Phenothiazine Derivatives", Journal of Pharmaceutical Sciences, vol. 53, No. 5, pp. 573-574 (1964).

I. Krzywiec, "Surface activity of guaiacol and some of its derivatives", Database CAPLUS on STN, AN 1970:36071, 1968.

Zeszyty naukowe uniwersytetu jagiellonskiego, prace chemiczne, 1964, No. 9, pp. 207-213.

T. Kita et al., "Profiles of an Intravenously Available Endothelin A-Receptor Antagonist, S-0139, for Preventing Cerebral Vasopasm in a Canine Two-Hemorrhage Model", Life Science, vol. 63, No. 4, pp. 305-315, 1998.

European Examination Report issued Apr. 16, 2009 in the corresponding European patent application EP 02 746 074.

* cited by examiner

INJECTABLE PHARMACEUTICAL FORMULATIONS

This application is a U.S. national stage of International Application No. PCT/JP02/07190 filed Jul. 16, 2002.

FILED OF THE INVENTION

The present invention relates to a process for suppressing the foaming which may occur at the time of the preparation of a solution or a suspension. Particularly, the present invention relates to pharmaceuticals, foods, and the like wherein the foaming at the time of the preparation of a solution or a suspension, which may cause any disadvantage, is suppressed.

BACKGROUND ART

The compound (compound 1) of formula:

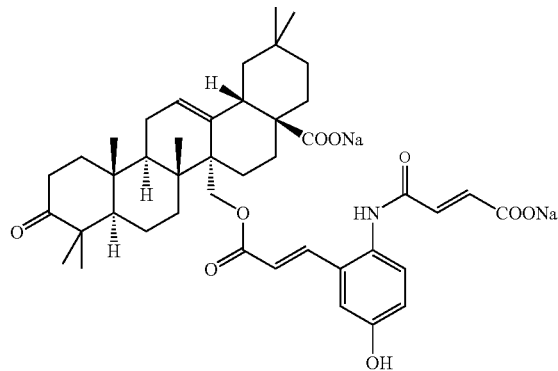

is a medicament for treating acute cerebro-vascular accidents such as intracerebral hemorrhage, cerebral infarction, and subarachnoid hemorrhage, and Japanese Patent Publication (kokai) No. 53484/1995 describes the same and related compounds as well as their preparations.

Compound 1 as described above is considered to be administered via intravenous infusion. In this case, a lyophilized formulation sealed closely in vials is first reconstituted or suspended in a water for injection or an infusion liquid therein, and then the solution or the suspension is mixed with an additional infusion liquid (about 100 to 500 ml, pH about 6 to 7) before use. However, vigorous mixing at the time of the dissolution/suspension in vials may cause the foaming, which has been recognized to lead to problems that it is difficult to transfer the whole contents of an effective ingredient into an additional infusion liquid, which would bring about a margin of error in dose, and that the foaming prevents from the reconstitution of the present compound when the dose is increased up to about 300 mg. Although it is possible to conduct the stirring smoothly on a table for example, such stirring would be an unpractical means in medical applications, showing that the suppression of foaming has been interested.

DISCLOSURE OF THE INVENTION

Under the circumstance, the inventors of the present application focused on the dissociation constant of compound 1, and found that the foaming is suppressed by adjusting the pH with a basic agent.

Japanese Patent Publication (kokai) No. 124481/1997 describes lyophilized formulations that are readily rendered clear, which is provided by using a vial coated with silicon as a formulation container to prevent the attachment of the foams that occur at the time of the resolution onto the inside of the vial. However, no foam suppression associated with pharmaceutical products has been reported. In industrial fields other than the pharmaceutical field, foams are suppressed by addition of silicons or alcohols, or foams are destroyed by mechanical means.

Specifically, as the first aspect, the invention provides:

an injectable pharmaceutical formulation which comprises an effective ingredient and a basic agent, wherein the effective ingredient meets the requirements:

1) it has a phenolic hydroxyl group;
2) its dissociation constant (pKa value) is 8 or more; and
3) the solution or the suspension containing the effective ingredient at a concentration of 30 to 40 mM shows a surface tension of 60 mN/m or less as determined by Wilhelmy method (solvent: water, determination temperature: 25° C.), and wherein the pH of the formulation in a state of solution or suspension is 8.5 or more; preferably, the pharmaceutical formulation, wherein the effective ingredient is a compound of formula (I):

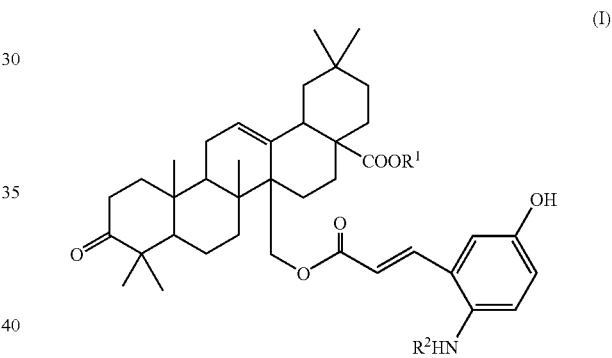

in which $R^1$ is a hydrogen, or a metabolizable ester residue; and $R^2$ is a hydrogen, or —$R^3$—$R^4$ wherein $R^3$ is —$SO_3$—, —$CH_2COO$—, —$COCOO$— or $COR^5COO$— wherein $R^5$ is a C1-C6 alkylene or a C2-C6 alkenylene, and $R^4$ is a hydrogen or a C1-C6 alkyl; or a pharmaceutically acceptable salt thereof, or a solvate of them; and As the second aspect, the invention provides:

a process for suppressing the foaming that occurs when a compound having a phenolic hydroxyl group is dissolved or suspended in an aqueous solvent, which comprises dissociating the phenolic hydroxyl group at the time of the dissolution or the suspension; preferably the process for suppressing the foaming, wherein the compound meets the requirements:

1) its dissociation constant (pKa value) is 8 or more; and
2) the solution or the suspension containing the compound at a concentration of 30 to 40 mM shows a surface tension of 60 mN/m or less as determined by Wilhelmy method (solvent: water, determination temperature: 25° C.); more preferably the process wherein a basic agent is used to allow the dissociation, even more preferably the process for suppressing the foaming, wherein the basic agent renders the pH of the solution or the suspension to be 8.5 or more; still even more preferably the process for suppressing the foaming, wherein the compound is a compound of formula (I) or a pharmaceutically acceptable salt thereof, or a solvate of them.

In a preferred embodiment, the invention provides the pharmaceutical formulation according to the first aspect, which comprises a 0.5 to 20 mg part of the basic agent relative to a 100 mg part of the effective ingredient. More preferably, the invention provides the pharmaceutical formulation according to the first aspect, which may be obtained by adding a 5 to 20 mg part of the basic agent to a 100 mg part of the compound of the formula (I) or a solvate thereof. In another preferred embodiment, the invention also provides the process for suppressing the foaming according to the second aspect, wherein the compound is a compound of formula (I) or a pharmaceutically acceptable salt thereof, or a solvate of them, and wherein a 0.5 to 20 mg part of the basic agent is added to a 100 mg part of the compound.

The present invention is suitable for an effective ingredient with a dissociation constant (pKa value) of 8 or more. Dissociation constant of effective ingredients may be determined by well-known methods such as potentiometric titration. It is preferred that the invention is applied to effective ingredients with a dissociation constant of 8 to 10, more preferably 8.5 to 9.5. The invention is not practically suitable for effective ingredients with a very high pKa value, since it is necessary to elevate the pH sufficiently to dissociate a phenolic hydroxyl group, which requires an additional step for pH rearrangement before administration. On the other hand, when effective ingredients with a very low pKa value are dissolved or suspended, then no foaming occurs, in which the invention is not necessary.

As used herein, "surface tension as determined by Wilhelmy method" means a surface tension obtained by dissolving or suspending an effective ingredient solely in a water to provide a solution or a suspension at a concentration of 30 to 40 mM, and determining the solution or the suspension for surface tension at 25° C. by Wilhelmy method. Effective ingredients that lead to a surface tension of 60 mN/m or less, preferably 50 to 60 mN/m as determined by Wilhelmy method may be applied to the present invention. Effective ingredients that lead to a high surface tension hardly induce relatively the foaming, creating no problem, whereas effective ingredients that lead to a low surface tension are more likely to induce the foaming, which induction of the foaming might not be suppressed by the present invention practically.

Wilhelmy method is well-known as a method for determining surface tensions (Bussei Butsuri Kagaku (Nankodo), K122 Determination of Surface Tension, CMC and Synergic Effects Users Manual (Kruess)). According to the method, a clean glass or thin metal plate is hung vertically and the end of the plate is submerged into a liquid, followed by determining the force that the plate is drawn downward.

As used herein, preferred effective ingredients are a compound of formula (I) or a pharmaceutically acceptable salt thereof, or a solvate of them.

In the formula, a metabolizable ester residue means any ester residue that is subjected to chemical or metabolic decomposition to provide a pharmacologically active compound in living bodies. Preferred ester residues include simple aliphatic or aromatic esters derived from the acidic groups of the original compounds. More preferred ester residues are C1-C6 alkyl esters of the acidic groups (for example, methyl esters, and ethyl esters). If necessary, double-ester type prodrugs may be prepared such as (acyloxy)alkyl ester, and ((alkoxycarbony)oxy)alkyl ester.

"C1-C6 Alkylene" means a straight or branched alkylene group having one to six carbon atoms, and includes, for example, methylene, ethylene, trimethylene, tetramethylene, and hexamethylene.

"C2-C6 Alkenylene" means a straight or branched alkenylene group having two to six carbon atoms, and preferred examples thereof are a group of —(CH=CH)m— wherein m is an integer of 1 to 3.

"C1-C6 Alkyl" means a straight or branched alkyl group having one to six carbon atoms, and includes, for example, methyl, ethyl, n-propyl, i-propyl, n-butyl, i-butyl, s-butyl, t-butyl, n-pentyl, i-pentyl, neopentyl, s-pentyl, t-pentyl, n-hexyl, neohexyl, i-hexyl, s-hexyl, and t-hexyl.

"Pharmaceutically acceptable salts" of a compound of the effective ingredient are salts obtained by the reaction with a suitable organic or inorganic acid, or a suitable organic or inorganic base. Salts formed with inorganic acids include salts with hydrochloric acid, hydrofluoric acid, hydrobromic acid, nitric acid, sulfuric acid, phosphoric acid, perchloric acid, hydriodic acid, and the like. Salts formed with organic acids include salts with formic acid, acetic acid, trifluoroacetic acid, fumaric acid, oxalic acid, tartaric acid, maleic acid, citric acid, succinic acid, malic acid, mandelic acid, ascorbic acid, lactic acid, and the like. Examples of organic bases include triethylamine and pyridine. Examples of inorganic cases include alkaline metals such as sodium and potassium, and alkaline-earth metals such as calcium and magnesium. Solvates include those formed with organic solvents and/or water, and may be coordinated with any number of solvent molecule for one molecule of a compound of effective ingredient.

As used herein, basic agents are not limited to specific species as long as they render the pH of a solution or a suspension containing an effective ingredient 8.5 or more. Specific examples include sodium hydroxide, potassium hydroxide, and calcium hydroxide. Amounts of basic agents are preferably 0.5 to 20 mg for 100 mg of effective ingredient. The pH of a solution or a suspension of an effective ingredient comprising a basic agent is 8.5 or more, preferably 9 to 9.8.

Amounts of basic agents "comprised" in a pharmaceutical formulation of the present invention are denoted as the amount of basic agents that is added relatively to 100 mg of effective ingredient, and the denotation are not affected by the subsequent changes in the amounts due to the formation of salts with phenolic hydroxyl groups.

"Solution or suspension" includes a state or a condition in which an effective ingredient has been dissolved or suspended in a suitable aqueous solvent. Preferably 10 to 500 mg, more preferably 100 to 400 mg, still more preferably 250 to 350 mg of a effective ingredient is dissolved or suspended in 1 to 500 ml, preferably 1 to 50 ml, more preferably 5 to 20 ml of an aqueous solvent to provide a solution or a suspension. Aqueous solvents are preferably water for injection, infusion liquids such as physiological saline, amino acids-containing infusion, and buffers such as phosphate buffers, and more preferred examples include water for injection or infusion liquids having pH 5 to 6.

For example, in case that an effective ingredient is a compound of formula (I) or a pharmaceutically acceptable salt thereof, or a solvate of them, a solution or a suspension having pH 8.5 or more is obtained by one of the following processes;

(A) A 0.5 to 5 mg part, preferably a 1 to 3 mg part, more preferably a 1.5 to 2.5 mg part of a basic agent is added to a 100 mg part of a compound (I) or a pharmaceutically acceptable salt thereof, or a solvate of them, preferably compound 1; and (B) A 5 to 20 mg part, preferably a 10 to 20 mg part, more preferably a 12 to 18 mg part of a basic agent is added to a 100 mg part of a compound (I) or a solvate thereof, preferably a free acid wherein the two COONa groups on compound 1 are both COOH groups (compound 2). Both pharmaceutical formulations as prepared according to processes (A) and (B) are fallen within "pharmaceutical formulations which comprise a 0.5 to 20 mg part of a basic agent relative to a 100 mg part of an effective ingredient".

As described above, the same pharmaceutical formulations can be prepared by various processes including not only a process which comprises adding a basic agent to a compound as an intended effective ingredient, but also processes which comprise adding different salt forms of compounds including also free compounds such as free acids with a basic agent in amounts according to the salt forms.

In case of the administration via intravenous infusion, an effective ingredient may be administered after preparing it to a solution or a suspension in vials, and then transferring it to infusion solution bags, and, in this case, even if the pH in the infusion solution bags is made 8.5 or less, that causes no problem since the object of the present invention has been achieved.

In the present invention, pharmaceutical formulations can be any dosage form as long as a solution or a suspension gives a pH of 8.5 or more. In other words, the pharmaceutical formulations of the present invention include solutions, suspensions, and lyophilized formulations including kit formulations for infusion such as double bag type kit formulations.

The present invention also provides pharmaceutical formulations which further comprises a saccharide such as glucose, maltose, lactose, sucrose, fructose and mannitol (preferably mannitol), or an amino acid, preferably a neutral amino acid, preferably glycine, alanine (more preferably alanine). It is preferred that the content of saccharide is 25% (w/w) or more relative to the effective ingredient, more preferably 40% to 60% (w/w), even more preferably 50% (w/w). This suppresses the decomposition of an effective ingredient. There is no upper limit in amounts of a saccharide or an amino acid to suppress the decomposition of an effective ingredient, although an excessive amount of a saccharide or an amino acid may react with an effective ingredient to produce new side-products.

A process for suppressing the foaming according to the present invention can be utilized in any case in which the foaming is disadvantageous such as the pharmaceutical field, as well as food and chemical fields. In other words, the present invention can be utilized in any case in which the foaming that occurs when a compound is dissolved or suspended in an aqueous solvent should be suppressed, which compound 1) has a phenolic hydroxyl group, 2) shows a dissociation constant (pKa value) of 8 or more, and 3) causes a surface tension of 60 mN/m or less as determined by Wilhelmy method (solvent: water, determination temperature: 25° C.) when dissolved or suspended at a concentration of 30 to 40 mM.

Aqueous solvents as used herein typically include water, infusion liquids such as a physiological saline, and an amino acids-containing infusion, buffers, water for injection, and preferably water for injection and infusion liquids.

According to the present embodiment, the present invention provides a process for suppressing the foaming that occurs at storage, which comprises dissociating the phenolic hydroxyl group. Preferred method for dissociations include the use of basic agents, more preferably sodium hydroxide, potassium hydroxide, and calcium hydroxide.

BEST MODE FOR CARRYING OUT THE INVENTION

1) Wilhelmy Method

Figure 1:
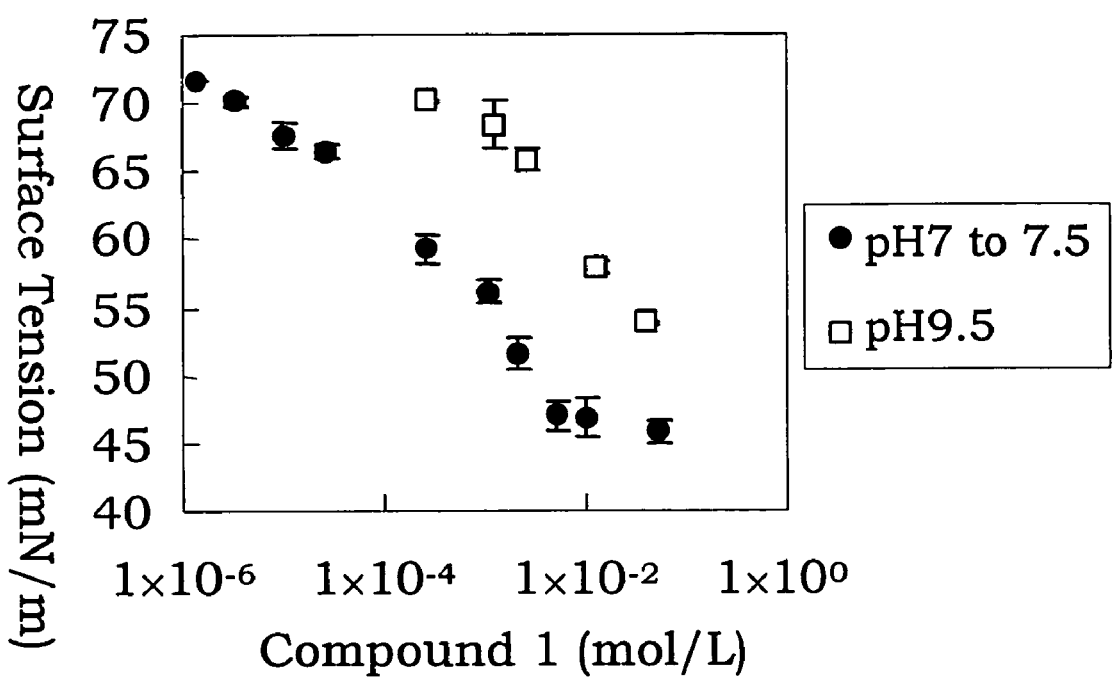
FIG. 1 is a graph showing the relationship between the concentration and the surface tension of compound 1 at pH 7 to 7.5, and pH9.5.
Figure 2:
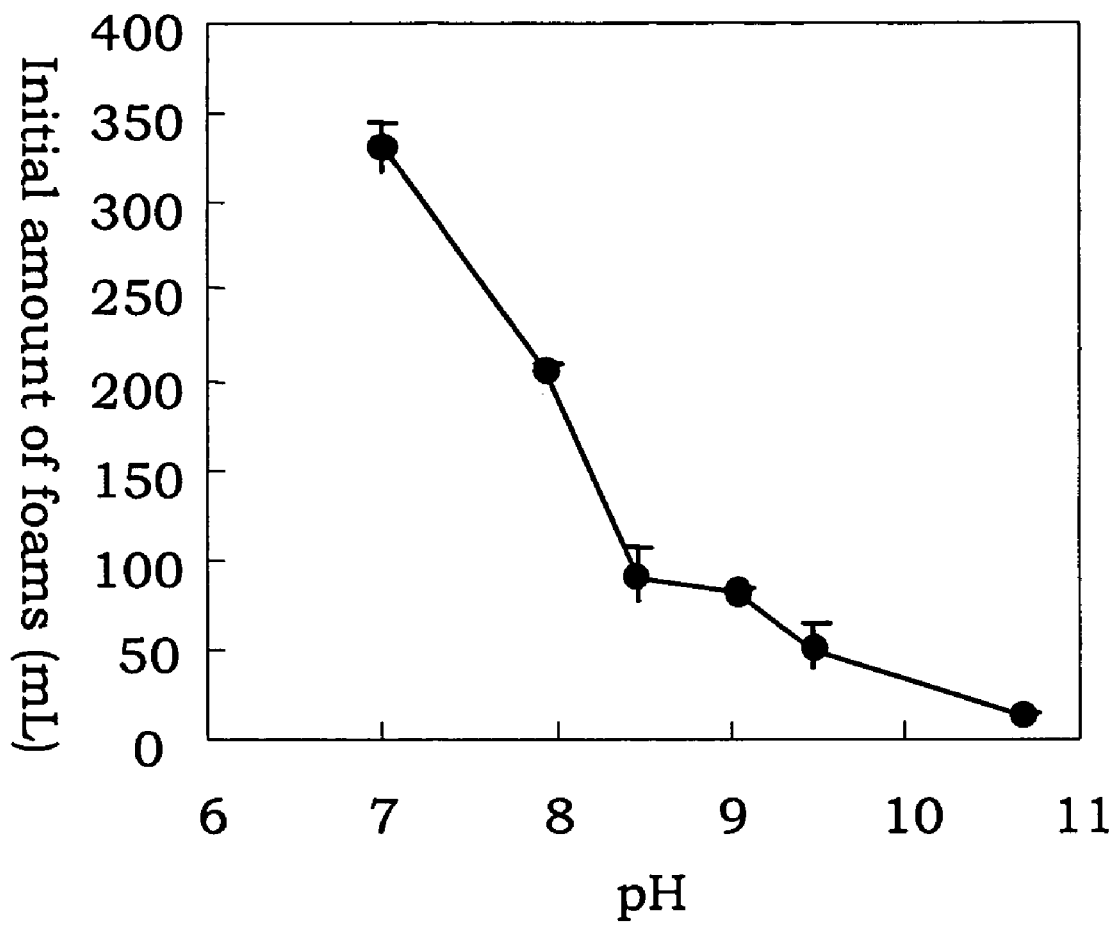
FIG. 2 is a graph showing the relationship between the amount of the foaming and pH as determined by Ross-Miles Foaming Test.

Ingredient for which the present invention is suitable can be selected by Wilhelmy method as described below.

Preparation of Samples to be Tested

A compound to be determined that has been weighed is dissolved or suspended in a defined amount of a distilled water. As such, samples of aqueous solutions to be tested containing the compound at various concentrations are prepared, and each of the solutions is adjusted to be 50 ml aliquots.

Setup of Determination Device

Surface tension-measuring device (Kruess Inc., Type K12) and the personal computer for control and analysis are started, and a software for determining surface tension (Kruess Inc., K122) is launched. The determination site of the device is subjected to the circulation of the water from a thermostatic chamber to keep the temperature constant at 25° C. The glass vessel (diameter: 65 mm, height: 40 mm) into which a sample to be tested is placed is washed thoroughly with water, and finally washed with acetone, thus being dried for use.

Setup of Plate for Determination

Plate as used for the determination is usually made of platinum, and assumes a rectangular shape of 19 mm in width, 10 mm in height, and 0.2 mm in thickness. The plate is burnt over a gas burner in order to remove residual materials attached to the surface before the start of the determination. On each determination of the sample to be tested, plate is washed with a distilled water and acetone, and dried.

Blank Determination

Forty ml of a distilled water is poured into the vessel that have been washed, and the vessel is placed into the surface tension-measuring device. Using the automatic detection function of the device, the end of the plate is submerged into the water up to 2 mm in depth from the surface of the water. In this condition, surface tensions are determined. Graphs of surface tensions versus time is displayed on the PC. When the value of surface tension as determined one minute later is almost constant, then the value is recorded and the determination is stopped.

Sample Determination

After the blank determination, 40 ml of a sample of aqueous solutions is poured into the vessel that have been washed, and the vessel is placed into the surface tension-measuring device. Using the automatic detection function of the device, the end of the plate is submerged into the sample up to 2 mm in depth from the surface of the sample. In this condition, surface tensions are determined. Graphs of surface tensions versus time is displayed on the PC. When the value of surface tension as determined one minute later is almost constant, then the value is recorded and the determination is stopped. When the value changes and is not constant, then the determination is continued until the value is constant, which constant value is in turn recorded.

2) Pharmaceutical Formulations

Pharmaceutical formulations of the present invention may be prepared by conventional methods according to dosage forms. In case of the preparation of injectable formulations, the following process may be adapted.

Instruments and materials as used in the preparation are preliminarily sterilized by conventional methods such as autoclaving, dry heat sterilization, and gamma ray-sterilization, in light of the form, the heat resistance, and the pressure tightness of the subject to be sterilized.

An effective ingredient and a saccharide if necessary that have been weighed are placed into a container for injection, and an appropriate amount of a solvent such as water for injection is added thereto, after which the mixture is stirred to prepare a solution or a suspension. The concentration of the effective ingredient in the solution or the suspension may be defined in light of the kinds of the solvent, solubility of the effective ingredient to the solvent, and the concentration at the time of reconstitution. Further, a basic agent is added for example in a form of 0.1 to 10 mol/L, preferably 1 mol/L aqueous solution so as to adjust the pH to 8.5 or more.

The solution or suspension thus obtained is sterilized by filtration according to conventional methods. If necessary, rough filtration may be conducted to remove the decomposed materials and contaminants before the sterilization by filtration.

The liquid sterilized by filtration is portioned into vials as appropriate, and lyophilized to give intended injectable formulation.

EXAMPLES

The following examples and test examples are presented for purpose of further illustration of the invention, and such examples are not intended to be limiting the invention in any respect.

Test Example 1

Determination of Surface Tension of Compound 1

The inventors assumed the foaming in compound 1 be caused predominantly by the surface activity of compound 1, and therefore the surface tension of the aqueous solution of compound 1 was determined by Wilhelmy method (Hanging plate method) (Bussei Butsuri Kagaku (Nankodo), K122 Determination of Surface Tension, CMC and Synergic Effects Users Manual (Kruess)).

Compound 1 was dissolved in a distilled water to prepare each 50 ml of aqueous solutions containing compound 1 in various concentrations.

Surface tension-measuring device (Kruess Inc., Type K12) and the personal computer for control and analysis ware started, and a software for determining surface tension (Kruess Inc., K122) was launched. The determination site of the device was subjected to the circulation of the water from a thermostatic chamber to keep the temperature constant at 25° C. The glass vessel (diameter: 65 mm, height: 40 mm) into which a sample to be tested was placed was washed thoroughly with water, and finally washed with acetone, thus being dried for use.

The plate that was made of platinum, and assumed a rectangular shape of 19 mm in width, 10 mm in height, and 0.2 mm in thickness was used for the determination. The plate was burnt over a gas burner in order to remove residual materials attached to the surface before the start of the determination. On each determination of the sample to be tested, plates were washed with a distilled water and acetone, and dried.

At first, blank determination was conducted. Forty ml of a distilled water was poured into the vessel that had been washed, and the vessel was placed into the surface tension-measuring device. Using the automatic detection function of the device, the end of the plate was submerged into the water up to 2 mm in depth from the surface of the water. In this condition, surface tensions were determined. Graphs of surface tensions versus time was displayed on the PC. The value of surface tension as determined one minute later was almost constant, and therefore the value was recorded and the determination was stopped. The determination was repeated twice, and the average was estimated.

Subsequently, sample determination was conducted. Forty ml of each sample of the aqueous solutions containing compound 1 in various concentrations (aqueous solution of compound 1, pH7 to 7.5) was poured into the vessel that had been washed, and the vessel was placed into the surface tension-measuring device. Using the automatic detection function of the device, the end of the plate was submerged into the sample up to 2 mm in depth from the surface of the sample. In this condition, surface tensions were determined. Graphs of surface tensions versus time was displayed on the PC. When the value of surface tension as determined one minute later was almost constant, then the value was recorded and the determination was stopped. When the value changes and was not constant, then the determination was continued until the value was constant (over 1 to 2 minutes), which constant value was in turn recorded. The determination was repeated twice, and the average was estimated.

Average values of surface tension (n=2) obtained as the results were plotted against each of logarithmic concentrations.

Further, aqueous solution containing compound 1 at various concentrations, which were adjusted to pH 9.5 with sodium hydroxide were determined for surface tension. The relationship between the surface tension at pH7 to 7.5 and pH9.5, and the concentrations of compound 1 is shown in FIG. 1.

The results of the determination of surface tension showed that the decrease in the surface tension is inhibited at pH 9.5 more than that at pH7 to 7.5.

The value of surface tension in the 37.6 mM solution of compound 1 at 25° C. was 53.9±0.2 mN/m.

Example 1

Fifteen hundreds g of a water for injection was added to 100.7 g of the bulk of compound 1 (90.0 g of the net content of compound 1) as prepared according to the process described in Japanese Patent Publication (kokai) No. 53484/1995 and 45.0 g of D-mannitol, and those solutes were dissolved, after which the solution was thoroughly stirred until turning transparently pale yellow. After the dissolution, the pH of the solution was determined while 1 mol/L aqueous sodium hydroxide was added drop by drop. At the time when the pH of the solution reached 9.5, the addition of aqueous sodium hydroxide was stopped (total added amount of the aqueous solution was 55 g), and an additional water for injection was added thereto until the total weight of the solution was 1800.0 g. The preparation liquid was roughly filtered through 0.45 μm filters, and then filtered through 0.22 μm filters to be sterilized. The sterilized filtrate was portioned into vials at 6.0 g (within ±1%) per vial, and lyophilized. The lyophilization of the filtrates was conducted by preliminarily freezing at −40° C., then primarily drying at −5° C. at 10 Pa for 24 hours or more, and secondarily drying at 60° C. at 2Pa for 5 hours. After the completion of the lyophilization, the vials were wound up with caps to prepare injectable formulations.

Example 2

To 3.81 g of compound 2 (4.00 g of the net content of compound 1), 2.00 g of d-mannitol and 64 g of 0.16 mol/L aqueous sodium hydroxide were added, and those solutes were dissolved. To the solution, 1 mol/L aqueous sodium hydroxide was added to adjust the pH 9.5 (total added amount of the aqueous solution was 4.79 g). An additional water for injection was added thereto until the total weight of the solution was 80.0 g, and the concentration was adjusted 50.0 mg/g. The preparation liquid was sterilized by filtration, and was portioned into vials at 2.00 g per vial, followed by being lyophilized. The lyophilized formulations comprise 100 mg of compound 1 (as 2 Na salt).

Test Example 2

Comparison in Foaming

Ten ml of a water for injection was added to the formulation as prepared in Example 1 or 2, and the mixture was shaken to facilitate the dissolution, during which the foaming was observed. Additionally, 100 mg of compound was dissolved in 10 ml of a water for injection to prepare the comparative formulation (pH 7.5), and the foaming was observed for comparison. The results are shown in the following table.

TABLE 1

| formulation | Formulation of Example 1 or 2 | Comparative formulation |
| --- | --- | --- |
| Foaming | The shaking caused a small amount of foaming, which disappeared within one minute. | The shaking caused the foaming that spread inside the whole vials, which did not disappear even after left for 24 hours. |

Test Example 3

Foaming of the Formulation Having a High pH Without Mannitol

To the formulation as prepared according to Example 1 except that no mannitol was added, 10 ml of a water for injection was added, and the mixture was shaken to dissolve the solutes, during which the foaming was observed. The shaking caused a small amount of foaming, but the foaming disappeared within one minute. The degree of foaming was similar to the formulation of Example 1 that was added with mannitol.

Test Example 4

Relationship Between Foaming and pH

Compound 1 was dissolved in a water for injection (0.1% w/w), and the solution was quantitatively determined for foaming by Ross-Miles Foaming Test. Ross-Miles Foaming Test was conducted according to the method as defined in International Standard ISO 696-1975 except that the determination temperature was set 25° C. The relationship between the foaming occurred in the present test and the pH is shown in Table 2. This shows that the foaming was inhibited depending on the increase in pH.

Example 3

Effect of Mannitol on Inhibition of Decomposed Materials Production

After the formulation as prepared according to Example 1 was stored at 50° C. for 2 months, the amounts of decomposed materials produced by hydrolysis were determined and compared. Typical decomposed materials are:

compound A compound B

The relationship of the contents of compound 1, the amounts of the decomposed materials, and the added amounts of D-mannitol comprised in between the formulation before the storage and that after the storage at 50° C. for 2 months, is shown in Table 2. The determination was conducted using high performance liquid chromatography (HPLC). The determination conditions of HPLC are as shown below:

Device: Waters 600E,484,712 wisp,74 1,FD20A
Column: J'sphere ODS-L80, S-4μm, 80A 150×4.6 mmφ
Moving phase: water/acetonitrile/acetic acid=100/100/1
Flow rate: 1.0 ml/min
Injected volume:
   20 μL (at the time for determination of impure materials)
   10 μL (at the time for determination of compound 1)
Detection wavelength
   275 nm
Detection sensibility (AUFS):
   0.64 (at the time for determination of impure materials)
   0.20 (at the time for determination of compound 1)
Solvent for dilution of samples:
   water/acetonitrile/acetic acid=100/100/1
Concentration of samples
   1 mg/ml (at the time for determination of impure materials)
   60.0 μg/ml (at the time for determination of compound 1)

TABLE 2

Effect of mannitol on the content of compound 1 and the amount of decomposed materials (%)

| | | 1 Added amount of D-mannitol (% of the weight of compound 1) | | | |
|---|---|---|---|---|---|
| | | 0% | 25% | 50% | 100% |
| Content of compound 1 (after storage at 50° C. for 2 months) | | 97.1 ± 0.1 | 97.9 ± 0.4 | 98.0 ± 0.1 | 98.3 ± 0.1 |
| compound A | Before storage | 0.26 ± 0.02 | 0.13 ± 0.01 | 0.11 ± 0.01 | 0.11 ± 0.01 |
| | After storage at 50° C. for 2 months | 1.71 ± 0.08 | 0.44 ± 0.01 | 0.24 ± 0.01 | 0.23 ± 0.02 |
| Other related compounds | Before storage | 0.32 ± 0.02 | 0.33 ± 0.03 | 0.32 ± 0.02 | 0.31 ± 0.01 |
| | After storage at 50° C. for 2 months | 0.66 ± 0.14 | 0.87 ± 0.02 | 0.89 ± 0.05 | 1.24 ± 0.05 |

Table 2 shows that the addition of D-mannitol suppressed the production of a decomposed product, compound A. Also, this suggested that the decrease in the content of compound 1 was suppressed.

INDUSTRIAL APPLICABILITY

A process for suppressing the foaming according to the present invention can be utilized at the time of the preparation of solutions or suspensions of foods and pharmaceuticals, and is useful for convenient preparation or manufacture of food products, and for accurate administration of pharmaceutical products.

The invention claimed is:

1. An injectable pharmaceutical formulation which comprises the compound of formula (I):

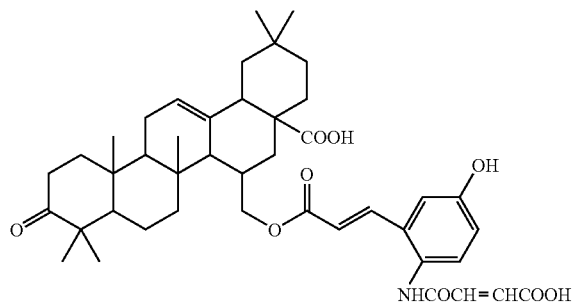

(I)

or a pharmaceutically acceptable salt thereof, mannitol and a basic agent, wherein the basic agent is sodium hydroxide, and
wherein the pH of the formulation in a state of solution or suspension is 8.5 to 9.8, and wherein foaming is suppressed.

2. The pharmaceutical formulation according to claim 1, wherein the formulation is lyophilized.

3. The pharmaceutical formulation according to claim 1, which is prepared by dissolving or suspending the pharmaceutical formulation in water for injection or an infusion, wherein in the formulation is lyophilized.

4. The pharmaceutical formulation according to claim 3, wherein the formulation is dissolved or suspended in 5 to 20 ml of water for injection or an infusion liquid.

5. The pharmaceutical formulation according to claim 1, wherein the pH of the formulation in a state of solution or suspension is 9 to 9.8.

6. The pharmaceutical formulation according to claim 1, wherein the content of the mannitol is 25% (w/w) or more relative to the compound of formula (I).

7. The pharmaceutical formulation according to claim 6, wherein the content of the mannitol is 40% to 60% (w/w) relative to the compound of formula (I).

8. The pharmaceutical formulation according to claim 1, wherein decomposition of the compound of formula (I) is suppressed.

9. A process for suppressing the foaming of an injectable pharmaceutical formulation which comprises the compound of formula (I):

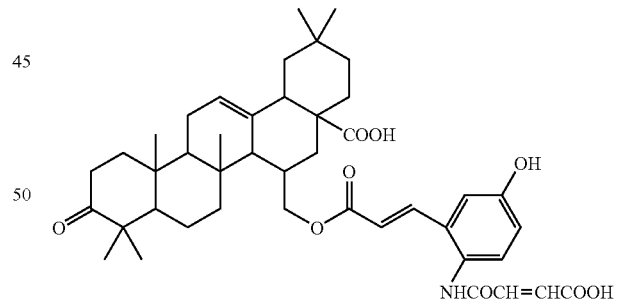

(I)

or a pharmaceutically acceptable salt thereof, mannitol and a basic agent, wherein the basic agent is sodium hydroxide, and
wherein the pH of the formulation in a state of solution or suspension is adjusted to 8.5 to 9.8.

10. The pharmaceutical formulation according to claim 1, comprising:
(A) 0.5 to 20 mg part of the basic agent relative to 100 mg part of a disodium salt of the compound of formula (I); or
(B) 12 to 18 mg part of the basic agent relative to 100 mg part of the compound of the formula (I).

* * * * *